(12) United States Patent
Bodduluri et al.

(10) Patent No.: US 7,621,933 B2
(45) Date of Patent: Nov. 24, 2009

(54) TOOL ASSEMBLY FOR HARVESTING AND IMPLANTING FOLLICULAR UNITS

(75) Inventors: Mohan Bodduluri, Palo Alto, CA (US); Paul K. Hsei, Huntington Beach, CA (US)

(73) Assignee: Restoration Robotics, Inc., Mountain View, CA (US)

( * ) Notice: Subject to any disclaimer, the term of this patent is extended or adjusted under 35 U.S.C. 154(b) by 569 days.

(21) Appl. No.: 11/421,438

(22) Filed: May 31, 2006

(65) Prior Publication Data

US 2007/0078475 A1 Apr. 5, 2007

Related U.S. Application Data (60) Provisional application No. 60/764,173, filed on Jan. 31, 2006, provisional application No. 60/753,602, filed on Dec. 22, 2005, provisional application No. 60/722,521, filed on Sep. 30, 2005.

(51) Int. Cl.
*A61B 17/34* (2006.01)
(52) U.S. Cl. ..................................... 606/187
(58) Field of Classification Search ................. 606/133, 606/187; 623/15.11
See application file for complete search history.

(56) References Cited

U.S. PATENT DOCUMENTS

| 3,867,942 A | 2/1975 | Bellantoni el al. |
| 3,998,230 A * | 12/1976 | Miller .................. 606/187 |
| 4,004,592 A | 1/1977 | Yamada |
| 4,160,453 A | 7/1979 | Miller |
| 4,451,254 A | 5/1984 | Dinius et al. |
| 4,476,864 A | 10/1984 | Tezel |
| 4,479,291 A | 10/1984 | Yamada |
| 4,716,901 A | 1/1988 | Jackson et al. |
| 4,751,927 A | 6/1988 | Yamada |
| 4,768,517 A | 9/1988 | Joachim |
| 4,969,963 A | 11/1990 | Honkura et al. |
| 5,036,860 A | 8/1991 | Leigh et al. |

(Continued)

FOREIGN PATENT DOCUMENTS

| DE | 10249786 | 5/2004 |
| EP | 524454 A1 * | 1/1993 |
| WO | WO 98/25666 | 6/1998 |

OTHER PUBLICATIONS

Inaba, M. And Inaba, Y., "Androgenetic Alopecia, Modern Concepts of Pathogenesis and Treatment", 29. Operative Treatment for Androgenetic Alopecia, Springer, 1996, pp. 238-244, 309. (9 pages).

(Continued)

*Primary Examiner*—Todd E Manahan
*Assistant Examiner*—Kevin Everage
(74) *Attorney, Agent, or Firm*—Lena I. Vinitskaya; Vista IP Law Group LLP (57) ABSTRACT

A multi-part tool assembly for harvesting and implanting follicular units, comprising an outer cannula having an open, tissue-piercing distal end, and an inner cannula coaxially positioned in a lumen of the first cannula, the second cannula having an open, tissue-coring distal end sized to engage and retain single hair follicular units. An obturator may be positioned in the lumen of the second cannula, wherein at least one of the first cannula, second cannula, and obturator are movable relative to the other ones.

15 Claims, 10 Drawing Sheets

U.S. PATENT DOCUMENTS

| | | |
|---|---|---|
| 5,050,608 A | 9/1991 | Watanabe et al. |
| 5,078,140 A | 1/1992 | Kwoh |
| 5,183,053 A | 2/1993 | Yeh et al. |
| 5,251,127 A | 10/1993 | Raab |
| 5,331,472 A | 7/1994 | Rassman |
| 5,395,368 A | 3/1995 | Ellman et al. |
| 5,417,683 A | 5/1995 | Shiao |
| 5,439,475 A | 8/1995 | Bennett |
| 5,483,961 A | 1/1996 | Kelly et al. |
| 5,490,850 A | 2/1996 | Ellman et al. |
| 5,562,613 A | 10/1996 | Kaldany |
| 5,578,054 A | 11/1996 | Arnold |
| 5,584,841 A | 12/1996 | Rassman |
| 5,584,851 A | 12/1996 | Banuchi |
| 5,611,810 A | 3/1997 | Arnold et al. |
| 5,611,811 A | 3/1997 | Goldberg |
| 5,662,661 A | 9/1997 | Boudjema |
| 5,693,064 A | 12/1997 | Arnold |
| 5,733,278 A | 3/1998 | Slatkine et al. |
| 5,782,843 A | 7/1998 | Aasberg |
| 5,782,851 A | 7/1998 | Rassman |
| 5,782,853 A | 7/1998 | Zeevi et al. |
| 5,792,163 A | 8/1998 | Hitzig |
| 5,792,169 A | 8/1998 | Markman |
| 5,817,105 A | 10/1998 | Van Der Brug |
| 5,817,120 A | 10/1998 | Rassman |
| 5,827,217 A | 10/1998 | Silver et al. |
| 5,827,297 A | 10/1998 | Boudjema |
| 5,858,019 A | 1/1999 | Ashraf |
| 5,865,744 A | 2/1999 | Lemelson |
| 5,873,888 A | 2/1999 | Costanzo |
| 5,893,853 A | 4/1999 | Arnold |
| 5,895,403 A | 4/1999 | Collinsworth |
| 5,899,916 A | 5/1999 | Casparian |
| 5,951,572 A | 9/1999 | Markham |
| 5,961,529 A | 10/1999 | Arnold |
| 5,984,936 A | 11/1999 | Mangubat et al. |
| 5,989,273 A | 11/1999 | Arnold |
| 5,989,279 A | 11/1999 | Rassman |
| 5,997,550 A | 12/1999 | Russell |
| 6,013,087 A | 1/2000 | Adams et al. |
| 6,027,512 A | 2/2000 | Bridges |
| 6,056,736 A | 5/2000 | Markman |
| 6,059,807 A | 5/2000 | Boudjema |
| 6,110,189 A | 8/2000 | Markman |
| 6,120,521 A | 9/2000 | Casparian |
| 6,445,943 B1 | 9/2002 | Ferre et al. |
| 6,461,369 B1 | 10/2002 | Kim |
| 6,547,782 B1 | 4/2003 | Taylor |
| 6,572,625 B1 | 6/2003 | Rassman |
| 6,585,746 B2 | 7/2003 | Gildenberg |
| 6,694,167 B1 | 2/2004 | Ferre et al. |
| 6,973,931 B1 | 12/2005 | King |
| 7,083,611 B2 | 8/2006 | Lemchen |
| 7,144,406 B2 | 12/2006 | Pak et al. |
| 7,172,604 B2 | 2/2007 | Cole |
| 7,201,722 B2 | 4/2007 | Krueger |
| 2001/0034534 A1 | 10/2001 | Transue |
| 2002/0103500 A1 | 8/2002 | Gildenberg |
| 2002/0133149 A1 | 9/2002 | Bessette |
| 2002/0151784 A1 | 10/2002 | Mizoguchi et al. |
| 2003/0040766 A1 | 2/2003 | Werner |
| 2003/0097144 A1* | 5/2003 | Lee ............................ 606/187 |
| 2003/0120298 A1* | 6/2003 | Gildenberg ................ 606/187 |
| 2004/0034282 A1 | 2/2004 | Quaid, III |
| 2004/0092924 A1 | 5/2004 | Vasa |
| 2004/0116942 A1 | 6/2004 | Feller |
| 2004/0193203 A1 | 9/2004 | Pak et al. |
| 2004/0220589 A1 | 11/2004 | Feller |
| 2004/0225314 A1 | 11/2004 | Fukuyama |
| 2005/0096687 A1 | 5/2005 | Rassman et al. |
| 2005/0187573 A1 | 8/2005 | Rassman et al. |
| 2005/0245952 A1 | 11/2005 | Feller |
| 2005/0267506 A1 | 12/2005 | Harris |
| 2006/0161179 A1 | 7/2006 | Kachenmeister |
| 2006/0178678 A1 | 8/2006 | Cole |
| 2006/0293703 A1* | 12/2006 | Pak et al. .................... 606/187 |

OTHER PUBLICATIONS

PCT International Search Report for PCT/US2006/0038002, Applicant Restoration Robotics, Inc., forms PCT/ISA/210 and 220, dated Apr. 11, 2007 (7 pages).

PCT Written Opinion of the International Searching Authority for PCT/US2006/0038002, Applicant Restoration Robotics, Inc., Form PCT/ISA/237, dated Apr. 11, 2007 (7 pages).

Riordan, Teresa, "Implanting hair is tedious, exacting work—the perfect work for a robot," The New York Times, Monday, Sep. 15, 2003 (1 page).

Harris, James, A., "New Methodology and Instrumentation for Follicular Unit Extraction: Lower Follicle Transection Rates and Expanded Patient Candidacy," Department of Otolaryngology/Head and Neck Surgery, Univ. Of Colorado Health Sciences Center, Denver, Colorado; Copyright 2006 by the American Society of Dermatologic Surgery, Inc. Published by BC Decker, Inc., Dermatologic Surgery, vol. 32, Jan. 1, 2006 (7 pages).

Annex to form PCT/ISA/206, Communication Relating to the Results of the Partial International Search, attached to PCT Invitation to Pay Additional Fees, PCT/ISA/206, for PCT/US2006/0038002, Applicant Restoration Robotics, Inc., dated Jan. 25, 2007 (5 pages).

* cited by examiner

TOOL ASSEMBLY FOR HARVESTING AND IMPLANTING FOLLICULAR UNITS

RELATED APPLICATION DATA

The present application claims the benefit under 35 U.S.C. § 119 to U.S. provisional patent application Ser. Nos. 60/722,521, filed Sep. 30, 2005, 60/753,602, filed Dec. 22, 2005, and 60/764,173, filed Jan. 31, 2006, which are all hereby incorporated by reference.

FIELD OF INVENTION

This invention relates generally to apparatus used for harvesting and implantation of hair follicular units.

BACKGROUND

Hair transplantation procedures are well-known, and typically involve (in a patient having male pattern baldness) harvesting donor hair grafts from the side and back fringe areas (donor areas) of the patient's scalp, and implanting them in a bald area (recipient area). Historically, the harvested grafts were relatively large (3-5 mm), although more recently, the donor grafts may be single follicular units. In particular, "follicular units" are naturally occurring aggregates of 1-3 (and much less commonly, 4-5) closely spaced hair follicles that are distributed randomly over the surface of the scalp. In one well-known process, a linear portion of the scalp is removed from a donor area by dissection with a scalpel down into the fatty subcutaneous tissue. The strip is dissected (under a microscope) into the component follicular units, which are then implanted into a recipient area in respective puncture holes made by a needle. Forceps are typically used to grasp and place the follicular unit grafts into the needle puncture locations, although other instruments and methods are known for doing so.

In "Androgenetic Alopecia" (Springer 1996), M. Inaba & Y. Inaba disclose and describe a method for harvesting singular follicular units by positioning a hollow punch needle having a cutting edge and interior lumen with a diameter of 1 mm, which is about equal to the diameter of critical anatomical parts of a follicular unit. The needle punch is axially aligned with an axis of a follicular unit to be extracted and then advanced into the scalp to cut the scalp about the circumference of the selected follicular unit. Thereafter, the follicular units are easily removed, e.g., using forceps, for subsequent implantation into a recipient site with a specially devised insertion needle.

Published U.S. Patent Application 20050203545 (Cole) discloses an instrument for the extraction of individual follicular units that purportedly allows for a more precise penetration depth and angle with respect to the skin surface of the skin of a patient.

Published U.S. Patent Application 20050267506 (Harris) discloses a method and apparatus for the extraction of follicular units by first scoring the outer skin layers with a sharp punch, and then inserting a separate blunt punch into the incision to separate the hair follicular unit from the surrounding tissue and fatty layer.

U.S. Pat. No. 6,585,746 (Gildenberg) discloses a hair transplantation system utilizing a robotic system, including a robotic arm and a hair follicle introducer associated with the robotic arm. A video system is used to produce a three-dimensional virtual image of the patient's scalp, which is used to plan the scalp locations that are to receive hair grafts implanted by the follicle introducer under the control of the robotic arm. The entire disclosure of U.S. Pat. No. 6,585,746 is incorporated herein by reference.

SUMMARY

In accordance with one aspect of the invention, a multi-part tool assembly is provided for the harvesting and implantation of hair follicular units in a body surface, such as a human scalp. In one embodiment, the tool assembly comprises a pair of coaxially disposed cannulas positioned in a reciprocating relationship, including an outer "implanting" cannula having an interior lumen and an open, tissue-piercing distal end, and an inner "harvesting" cannula positioned in the implanting cannula lumen. The harvesting cannula has an open, tissue-coring distal end, and an interior lumen sized to frictionally engage and retain a follicular unit.

The tool assembly may be hand-held and positioned. In the alternative, the tool assembly may be attached to, and positioned by, a moveable arm of an automated system, e.g., a robotic arm system. Movement of one or both of the harvesting and implanting cannulas relative to each other and/or to the remainder of the tool assembly (whether hand-held or carried by an automated positioning system) may be provided by a number of different mechanical, electromechanical, pneumatic, hydraulic, magnetic, and other known systems and mechanisms for effecting controlled movement of the respective cannulas. While the implanting and harvesting cannulas are preferably axially aligned, other embodiments are possible.

For harvesting, a longitudinal axis of the harvesting cannula is axially aligned with a longitudinal axis of a selected follicular unit to be harvested. Depending on the embodiment, positioning of the harvesting cannula relative to the selected follicular unit may be manual or fully automated. In one embodiment, an image-guided robotic system including a robotic arm is used to position and align the respective harvesting cannula and follicular unit. The harvesting cannula is advanced over the follicular unit, with its distal coring end penetrating the body surface into the subcutaneous fatty layer surrounding and underlying the follicular unit. The harvesting cannula is then withdrawn from the body surface to thereby extract the follicular unit, which is carried in the harvesting cannula lumen.

Movement of the harvesting cannula relative to the body surface may be manual, semi-automated, or completely automated. The harvesting cannula may be fixed or independently moveable relative to the remainder of the tool assembly, whether the tool assembly is hand-held or attached to a moveable arm. In embodiments in which the tool assembly is carried on an automated (e.g., robotic) arm, movement of the harvesting cannula relative to the body surface may be performed by movement of the arm relative to the body surface, movement of the harvesting cannula relative to the automated arm, or a combination of each. Similarly, in hand-held embodiments, movement of the harvesting cannula relative to the body surface may be performed by movement of the operator's arm relative to the body surface, movement of the harvesting cannula relative to the tool assembly, or a combination of each. In some embodiments, the harvesting cannula is rotated about its longitudinal axis as it penetrates the body surface to enhance its tissue-coring effectiveness.

In some embodiments, the wall of the harvesting cannula lumen may be textured in order to facilitate grasping and extracting the follicular unit. In some embodiments, a vacuum source may be selectively placed in communication with the harvesting cannula lumen to apply a proximally directed "pulling" force to facilitate grasping and extracting the follicular units. These features may also be helpful in retaining the follicular unit in the harvesting cannula lumen after it is harvested.

For implantation, the tool assembly is repositioned (whether manually or by using an automated system) to a selected implantation site in a recipient area on the body surface. A longitudinal axis of the implanting cannula may be aligned with a desired orientation of the follicular unit, when implanted. Again, this alignment may be performed manually or by an automated system, e.g., by using an image-guided robotic system in one embodiment. The tissue-piercing distal end of the implanting cannula is advanced into the body surface, creating a subcutaneous implantation cavity of an appropriate depth and size for receiving a follicular unit being implanted. This "puncture motion" by the implanting cannula is preferably very rapid in order to minimize trauma to the tissue surface in the implantation cavity, e.g., akin to the motion of a spring-loaded finger pricking device used for obtaining small amounts of blood for testing.

In one embodiment, a follicular unit is moved axially from the harvesting cannula lumen (where it has remained undisturbed since it was harvested) into the distal end portion of the implanting cannula lumen by an obturator (plunger) disposed in the harvesting cannula lumen. This repositioning of the follicular unit may take place before, during, or after the implanting cannula punctures the body surface. The obturator thereafter maintains the relative position of the follicular unit in the implantation cavity as the implanting cannula is withdrawn from the body surface by translational movement relative to the obturator. In others embodiment, the follicular unit is deposited directly from the harvesting cannula lumen into the implantation cavity, e.g., by the obturator, or by applying a distally directed "pushing" force using a source of pressured air placed in communication with the harvesting cannula lumen.

Other and further embodiments, objects and advantages of the invention will become apparent from the following detailed description when read in view of the accompanying figures.

BRIEF DESCRIPTION OF THE DRAWINGS

Embodiments of the invention are illustrated by way of example and not limitation in the figures of the accompanying drawings, in which like references indicate similar elements, and in which.

DETAILED DESCRIPTION OF THE ILLUSTRATED EMBODIMENTS

Figure 1:
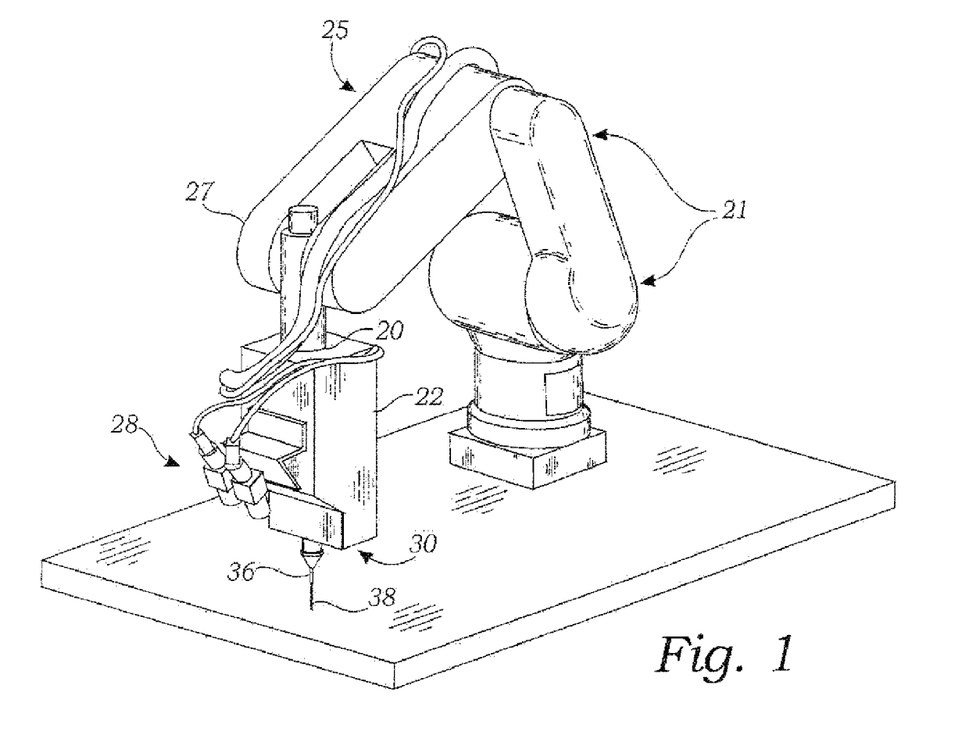
FIG. 1 is a perspective view of a robotic arm system used for positioning and orienting a pair of coaxially-disposed cannulas extending from a distal opening of a tool assembly housing carried by the robotic arm and used for harvesting and implanting human hair follicular units.
Figure 2:
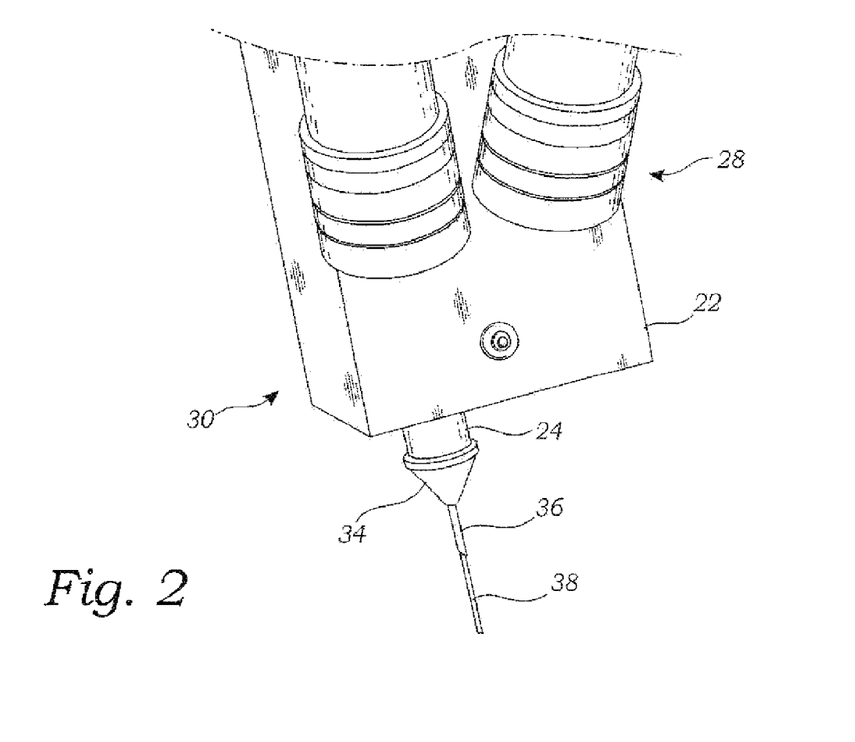
FIG. 2 is a close-up of the distal portion of the tool assembly housing shown in FIG. 1.

FIGS. 1 and 2 depict an image-guided robotics system 25, including a robotic arm 27 with a tool assembly 30 attached to a distal tool plate 20. The tool assembly 30 includes coaxially disposed harvesting and implanting cannulas 38 and 36, respectively, extending from a tubular extension 24 of a housing 22. The cannulas 36 and 38 are axially stiff, e.g., made of a hard metal or plastic, and thin-walled to facilitate tissue penetration. The implanting cannula 36 has a needle-like tissue piecing tip, and the harvesting cannula has a tissue-coring (e.g., serrated) tip.

Figure 3:
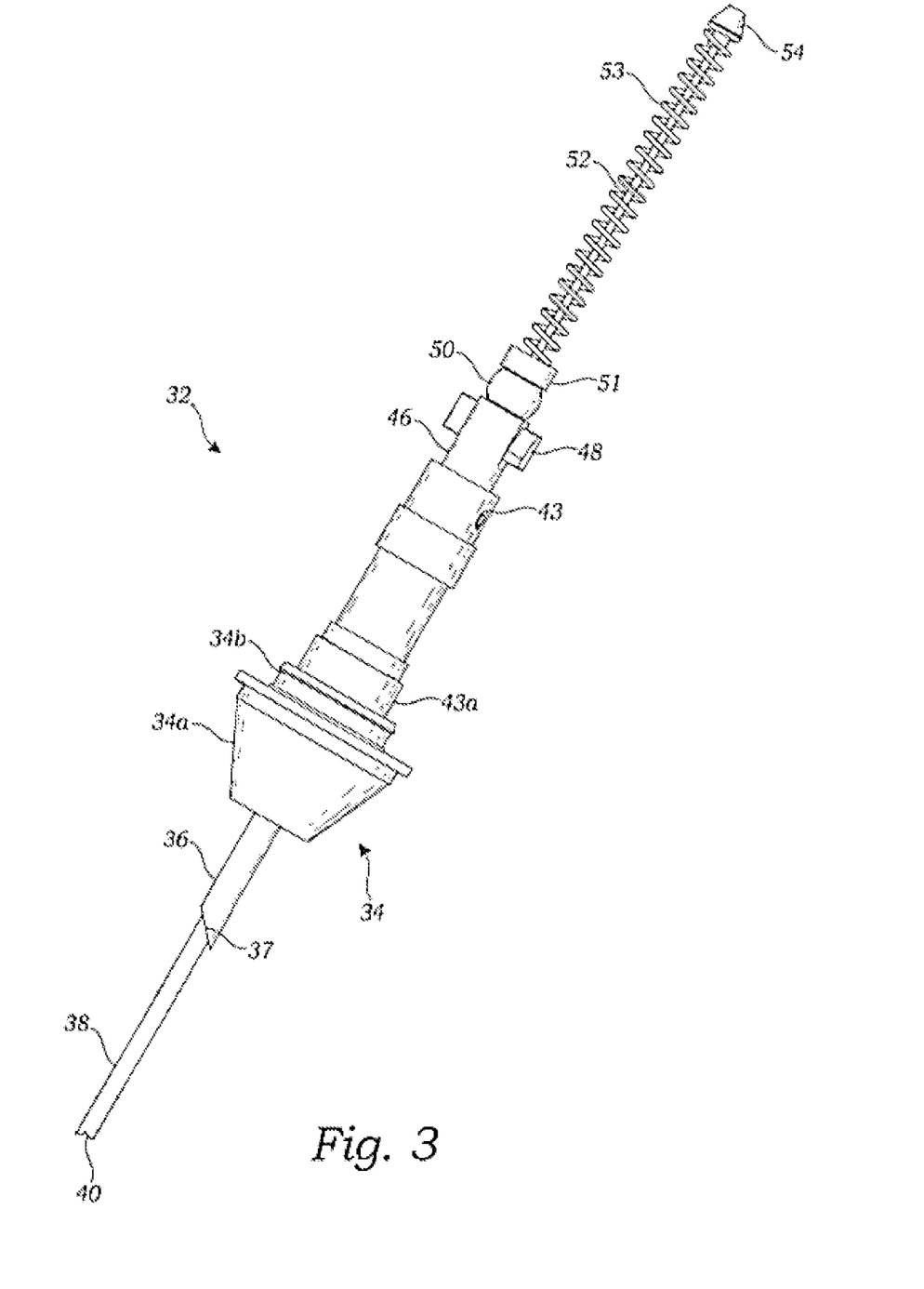
FIG. 3 is a perspective view of a multi-part tool for use in the tool assembly in the system of FIG. 1.

As described in detail the above-incorporated provisional application No. 60/764,173, the robotic arm 27 automatically and precisely positions the respective harvesting and implanting cannulas 38 and 36 at desired locations, and in desired orientations, along a body surface (e.g., a scalp) of a patient based on control signals derived at least in part from image data acquired by one or more cameras 28 attached to the tool assembly housing 22. Such automatic and precise positioning of the respective harvesting and implanting cannulas 38 and 36 is provided with a high degree of repeatability and accuracy (e.g., to 20 microns) by respective motors and encoders located in respective arm joints 21 of the robotic arm 27. Hair transplantation generally includes three steps: follicular unit harvesting, recipient site incision, and follicular unit placement in the incision. FIG. 3 shows one embodiment of a three-part tool 32 used for performing all three of these functions. Although the ensuing description of the three-pad tool 32 is with reference to its use as part of the tool assembly 30 carried on the robotic arm 27 in the system 25 of FIG. 1, it will be appreciated that hand-held and operated embodiments of the three-part tool 32 are also possible.

More particularly, the three-part tool 32 includes an outer ("implanting") cannula 36 having an open, tissue-piercing (e.g., beveled) distal end 37 used for making incisions at recipient (implantation) sites in a body surface. An inner ("harvesting") cannula 38 is coaxially positioned in an interior lumen of the implanting cannula 36, and has an open, tissue-coring (e.g., rough or serrated) distal end 40. The harvesting cannula 38 has an interior lumen appropriately sized for harvesting singular human hair follicular units by coring the respective follicular units and extracting them from a body surface (typically but not necessarily a scalp). By way of non-limiting examples, embodiments of the harvesting cannula 38 may have interior lumens that range from approximately 0.3 millimeters to 2.0 millimeters in diameter. In one embodiment, the harvesting cannula lumen has a diameter that is approximately 1 millimeter in diameter. Notably, different sized harvesting cannulas 38 may be used for harvesting single-follicle follicular units than for harvesting multi-follicle follicular units. In either case, an inner wall surface of the harvesting cannula lumen may be textured to facilitate frictional grasping the respective follicular units for extraction from the body surface after they are cored.

Figure 4:
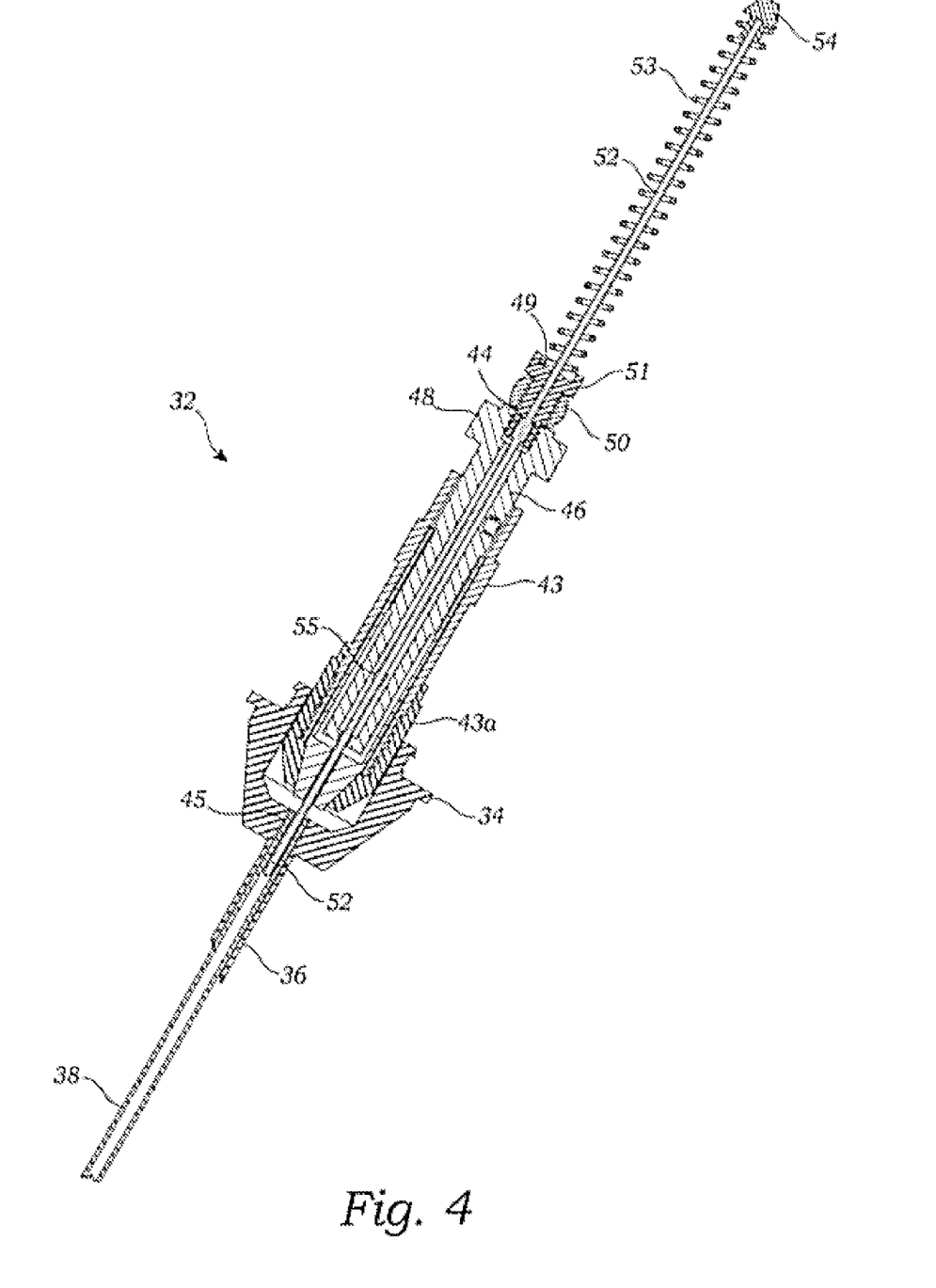
FIG. 4 is lengthwise sectional view of the multi-part tool of FIG. 3.
Figure 5:
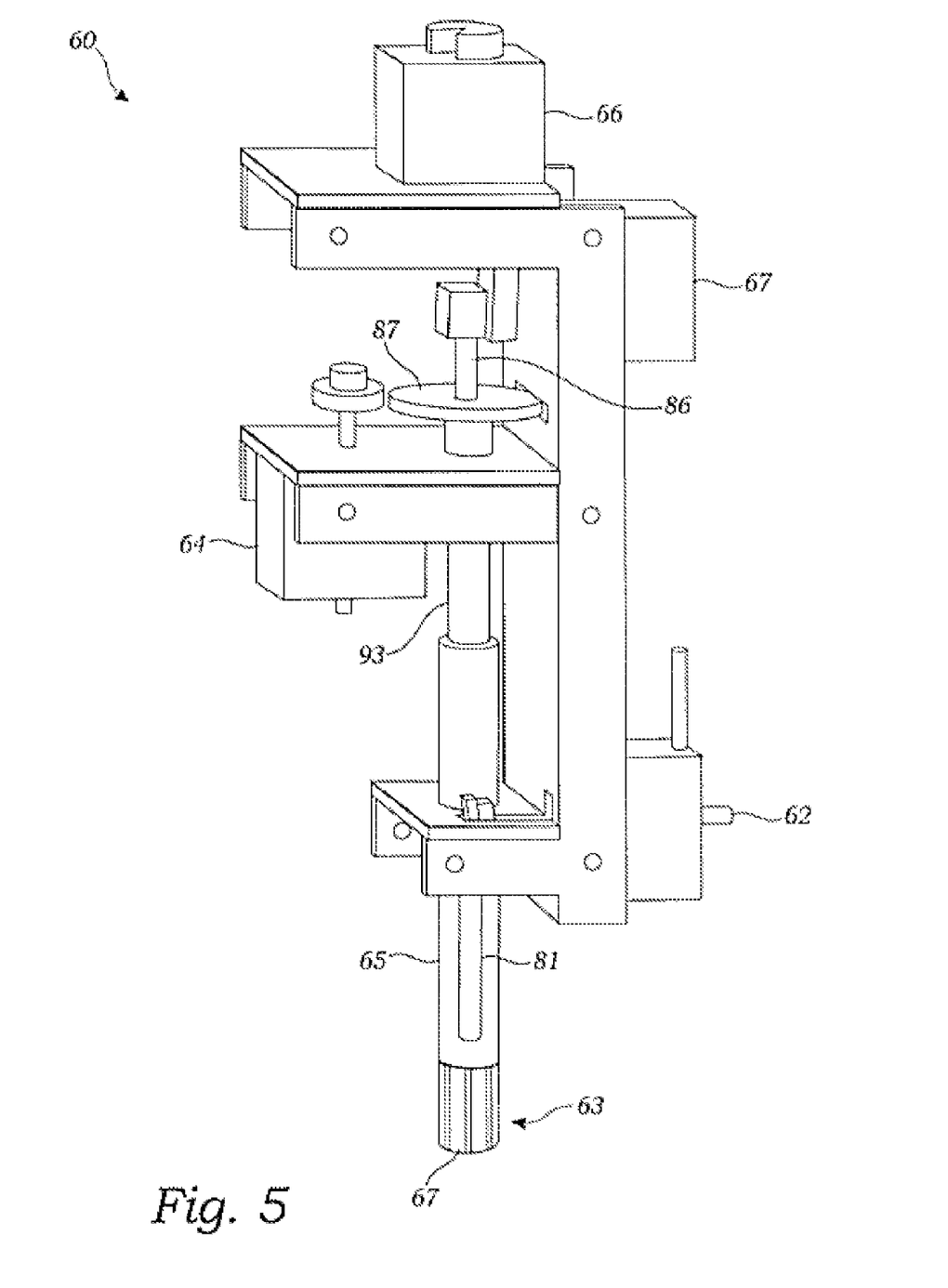
FIG. 5 is a perspective view of a motor drive assembly for operatively coupling with the multi-part-part tool of FIG. 3 in the tool assembly of the system of FIG. 1.

With reference also to FIGS. 4 and 5, the tool assembly 30 includes a motor drive assembly 60 mounted in the housing 22 and configured to receive and operatively engage the component parts of the three-part tool 32. In particular, the implanting cannula 36 is fixedly attached to a proximal hub 34, including a distal facing tapered portion 34a and a proximally directed engagement portion 34b. The engagement portion 34b may be detachably-coupled (snap-fit) with a resilient gripper 63 extending from a tubular sleeve 65 in the motor drive assembly 60. In the illustrated embodiment, the gripper 63 comprises a plurality of resilient arm members 67 that are attached to or integral with, the tubular sleeve 65. It will be appreciated that other detachable coupling mechanisms may be employed in alternate embodiments. The tubular sleeve 65 engages a rack-and-pinion drive mechanism 81 driven by a first motor 62 of the motor drive assembly 60, so that, when the hub 34 is coupled to the gripper 63, the motor 62/drive mechanism 81 provide axial (i.e., reciprocating) motion of the implanting cannula 36 relative to the harvesting cannula 38 (and also relative to the tool assembly housing 22/24).

The harvesting cannula 38 extends proximally through a bore 45 of the implanting cannula hub 34 and implanting cannula 36, and is fixedly attached to distal chuck portion 43a of a pin vise 43 seated in, and rotatable relative to, a bore of hub 34. An elongate body 46 is seated in, and fixedly attached to, the pin vise 43, and includes one or more radially-outward extending flanges 48 that engage a corresponding set of slots (not shown) in a distally projecting tubular drive member (not shown—extends internally through housing 93) coupled to an output gear 87 driven by a second motor 64 of the motor drive assembly 60 for thereby rotating the respective elongate body 65 and harvesting cannula 38, respectively, about a longitudinal axis of the harvesting cannula 38. As will be appreciated, a belt drive or other means for rotating the tubular drive member (and, thereby, the harvesting cannula 38) may be used in alternative embodiments. The elongate body 46 further includes a recessed section 44 located proximally of the flanges 48, which seats an annular retaining member 50 for detachably-coupling (via a snap-fit type connection) with the tubular drive member (proximal of the slots that engage flanges 48), thereby retaining the harvesting cannula 38 in position when the tool 32 is coupled with the motor drive assembly 60.

An elongate obturator 52 is slidably positioned in an interior lumen of the harvesting cannula 38, and has a proximal end attached to a seating member 54 that engages with a linear ("screw-drive") drive mechanism (not shown) driven by a third motor 66 of the motor drive assembly 60 for selectively providing a distally-directed, "pushing" force on the obturator 52 relative to the harvesting cannula 38. A spring 53 is seated in an annular recess 49 formed in a proximal end-cap 51 of the elongate body 46, and extends (over the obturator 52) to the distal side of the seating member 54. The spring 53 applies a proximally-directed, "pulling" force on the seating member, to thereby bias the obturator against the screw drive.

The drive motor assembly further includes a "release" motor 67, that applies a distally-directed (pushing) force against the end-cap 51 via a tubular release member 86, which causes the respective attachment couplings (i.e., the implanting cannula hub 34b and gripper 63, and the harvesting cannula retaining member 50 and the tubular drive member) to decouple for removal of the tool 32 from the tool assembly 30, e.g., for replacing one or both of the implanting and harvesting cannulas 36 and 38. In this manner, the multi-part tool 32 may be loaded into the tool assembly 30 by insertion (in the proximal direction) of the tool 32 ("back loaded") through the tubular extension 24 of the housing 22, until the respective couplings 34b and 50 snap into place with their counterparts in the motor drive assembly 60, and released by application of a sufficient force by the motor 67 on the release member 86 to decouple the respective couplings. A stop member 55 is attached to the obturator 52 that abuts the distal side of the end-cap as the release member 86 applies a downward force on the end-cap 51, so that the obturator 52 accompanies the rest of the tool 32 as it is released from the motor drive assembly 60 (and from the tool assembly 30).

The motor drive assembly 60 further comprises control circuitry for controlling operation of the respective motors 62, 64, 66, and 67. The control circuitry may include an independent processor (not shown) associated with the motor drive assembly 60, which receives as inputs information from the robotic system 25, including but not limited to positioning data obtained from images acquired of the respective cannulas 36, 38 and body surface/objects (e.g., hair follicles). Additionally or alternatively, a respective encoder may be operatively coupled with one or more of the motors 62, 64, 66, and 67 for tracking the relative movement and, thus, position information, of the implanting cannula 36, harvesting cannula 38, and/or obturator 52.

For harvesting a follicular unit from a body surface (e.g., a scalp), the robotic arm 27 positions and aligns the harvesting cannula 38 with a longitudinal axis of a selected follicular unit to be harvested. The harvesting cannula 38 is then advanced over the selected follicular unit by motion of the robotic arm 27, accompanied by simultaneous rotational movement of the harvesting cannula 38 about its longitudinal axis by the motor 64, with the open distal end 40 of the cannula 38 penetrating the body surface into the subcutaneous fatty layer surrounding and underlying the follicular unit. In alternate embodiments, a linear drive mechanism may be additionally provided in the motor drive assembly 60 for providing independently controlled axial translation of the harvesting cannula 38 relative to the tool assembly housing 20 (and implanting cannula 36). The harvesting cannula 38 is then withdrawn from the body surface by motion of the robotic arm 27 to thereby extract the follicular unit, which is carried in the lumen of the harvesting cannula. In some embodiments, a vacuum source may be selectively placed in communication with the harvesting cannula lumen to apply a proximally-directed "pulling" force to facilitate grasping and extracting the follicular unit, as well as to help retain the follicular unit in the harvesting cannula lumen after it has been harvested.

Figure 6A:
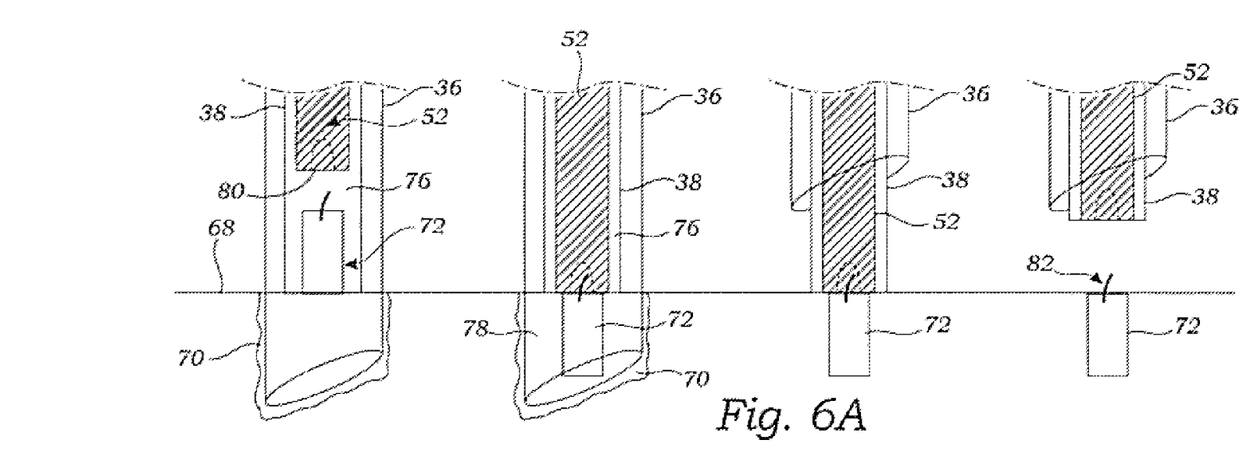
FIGS. 6A and 6B are simplified, partially cut-away views of alternative implantation procedures carried out using the three-part tool of FIG. 3.
Figure 6B:
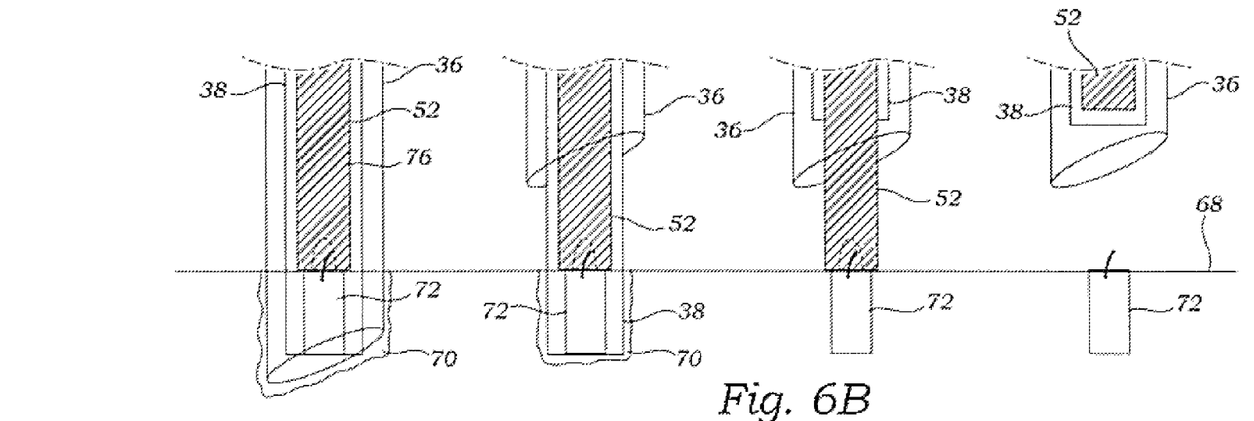

For implantation, the tool assembly 30 is repositioned by the robotic arm 27 to a selected implantation site on the body surface. At the implantation site, a longitudinal axis of the implanting cannula 36 is preferably aligned with a desired orientation of the follicular unit, when implanted. With reference to FIGS. 6A-B, the tissue-piercing distal end 37 of the implanting cannula 36 is advanced over the harvesting cannula 38 and into the body surface 68, creating a subcutaneous implantation cavity 70 of an appropriate depth and size for receiving the harvested follicular unit 72. This puncture motion by the cannula 36 is automatically controlled by motor 62, and is preferably very rapid in order to minimize trauma to the tissue surface 74 of the implantation cavity 70.

In one embodiment (shown in FIG. 6A), the follicular unit 72 is moved axially by the obturator 52 (under the control of motor 66) from the harvesting cannula lumen 76, where it has remained undisturbed since it was harvested, into a distal end portion of the implanting cannula lumen 78. This repositioning of the follicular unit 72 from the harvesting cannula lumen 76 into the implanting cannula lumen 78 may take place before, during, or after the implanting cannula 36 has punctured the body surface 68. The obturator thereafter maintains the follicular unit 72 in the implantation cavity 70 as the implanting cannula 36 is withdrawn from the body surface 68 by translational movement relative to the obturator 52. Once the implanting cannula 36 is withdrawn, the obturator 52 is also withdrawn, with the follicular unit 72 implanted in the body surface. A distal facing end 80 of the obturator 52 is preferably recessed to allow room for one or more hair follicles 82 protruding from the follicular unit 72.

In another embodiment (shown in FIG. 6B), the respective distal ends of the implanting and harvesting cannulas 36 and 38 are aligned (i.e., by relative movement of the implanting cannula 36) so that their respective distal ends 37 and 40 are approximately coextensive. This alignment of the respective cannula distal ends 37 and 40 may take place before, during, or after the implanting cannula penetrates the body surface to form the implantation cavity 70. Thereafter, the respective cannulas 36 and 38 are withdrawn from the implantation cavity 70, while the follicular unit 72 is retained therein, i.e., by simultaneous movement of the robotic arm 27 away from the body surface 68 and of the obturator 52 towards the body surface 68. In alternate embodiments having a linear drive mechanism in the motor drive assembly 60 for providing independently controlled axial translation of the harvesting cannula 38 relative to the tool assembly housing 20 (and implanting cannula 36), the respective cannulas 36 and 38 may be withdrawn from the implantation cavity 70 relative to (and without requiring simultaneous movement of) the obturator 52 by operation of the motor drive assembly 60. In other alternate embodiments, a source of pressurized air selectively placed in communication with the harvesting cannula lumen 76 may be used to retain the follicular unit 72 in the implantation cavity 70 as the cannulas 36 and 38 are withdrawn.

Figure 7:
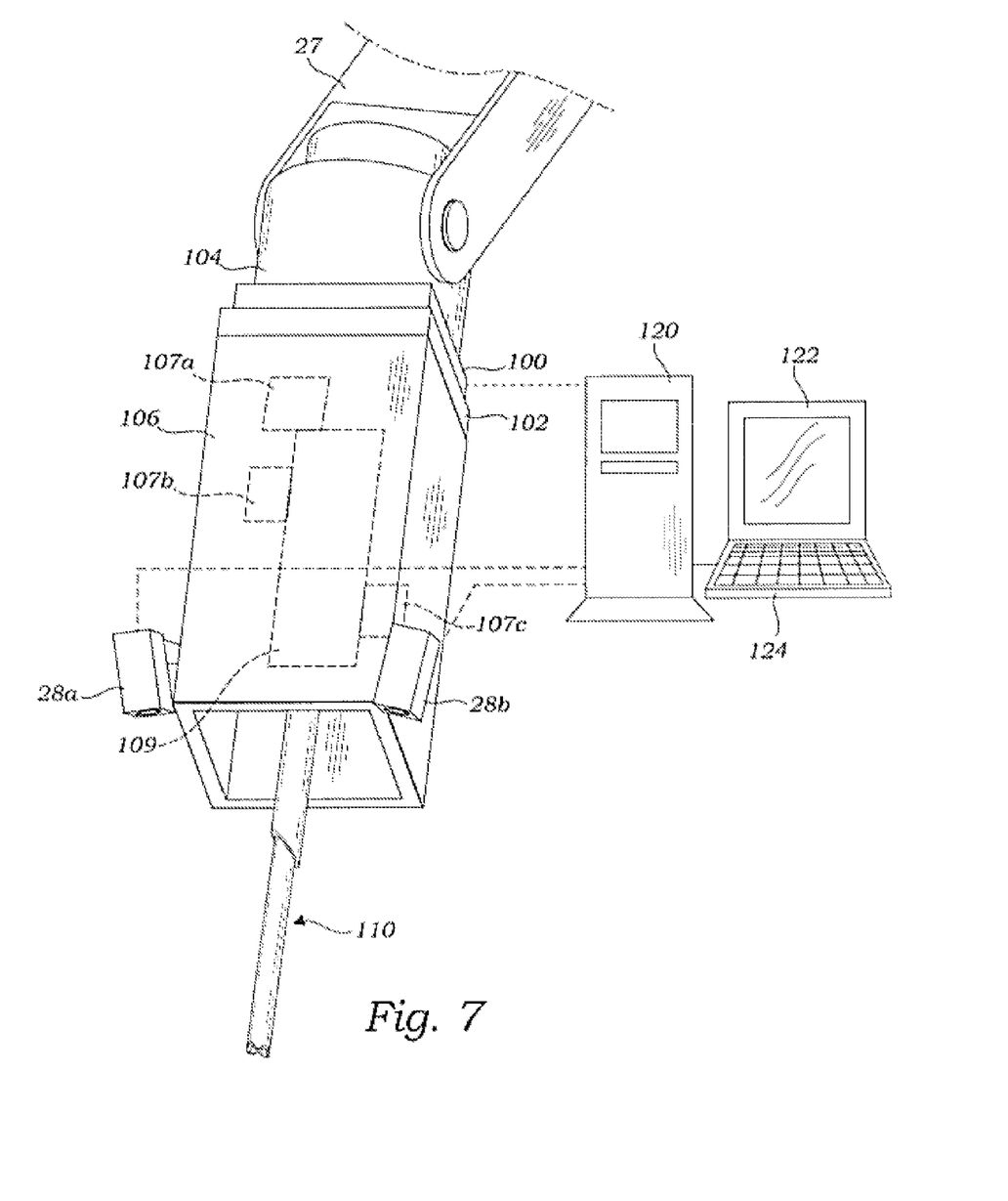
FIG. 7 is a partial-schematic, partial perspective view of one embodiment of the tool assembly of the robotic system in FIG. 1.

FIG. 7 illustrates a distal portion of the robotics system 25 in accordance with some embodiments of the invention. A force sensor 100 is secured to an arm 104, a plate 102 mounted to the force sensor 100, and a motor drive, or "positioning" assembly 106 secured to the plate 102. Alternatively, the plate 102 could be secured directly to the arm 104, in which cases, the force sensor 100 may be secured between the positioning assembly 106 and the plate 102. Alternatively, the force sensor 100 may be located within the positioning assembly 106. The force sensor 100 is configured to sense three forces Fx, Fy, Fz in three different orthogonal directions X, Y, Z, and three orthogonal moments Mx, My, Mz. In other embodiments, the force sensor 100 may be configured to sense one or two of the forces Fx, Fy, Fz, and/or one or two of the moments Mx, My, Mz. As shown in the figure, the force sensor 100 is coupled to a computer 120, which receives data from the force sensor 100 representing the sensed force(s) and/or moment(s). In other embodiments, the force sensor data may go directly to the robot.

During the above harvesting and implanting process, the force sensor 100 monitors one or more force/moment component transmitted from the positioning assembly 106. For example, the force sensor 100 may monitor a force Fz, which has a directional vector that is approximately parallel to an axis of a harvesting cannula 200. The sensed force Fz is transmitted to the computer 120, which determines whether a magnitude of the sensed force Fz is within an acceptable limit. In some embodiments, the computer 120 is configured (e.g., programmed) to stop a harvest process or an implant process if the sensed force Fz exceeds a prescribed limit, which may indicate that the harvesting cannula 200 or the implanting cannula 202 is pressing against the skull, for example. As such, the force sensor 100 provides a safety feature that prevents the harvesting cannula 200 and the implanting cannula 202 from injuring a patient in an unintended way.

In the illustrated embodiments, the positioning assembly 106 includes a holding unit 109 for engagement with a cannula assembly 110, and a plurality of positioners 107a-107c. The holding unit 109 is configured to engage with different parts of the cannula assembly 110 so that the cannula assembly 110, as a whole, can be positioned by the positioning assembly 106. The holding unit 109 also allows different components of the cannula assembly 110 to be controlled after the cannula assembly 110 is engaged with the holding unit 109. The positioners 107a-107c are configured for moving different components of the cannula assembly 110 after it has been engaged with the holding unit. Although three positioners 107a-107c are shown, in other embodiments, the positioning assembly 106 may include more or less than three positioners 107. In some embodiments, the positioning assembly 106 may include the motor drive assembly of FIG. 5, which includes three motors (positioners) for moving different components of the cannula assembly 110, plus an additional motor for disengaging the cannula assembly 110 from the positioning assembly.

Figures 8, 10:
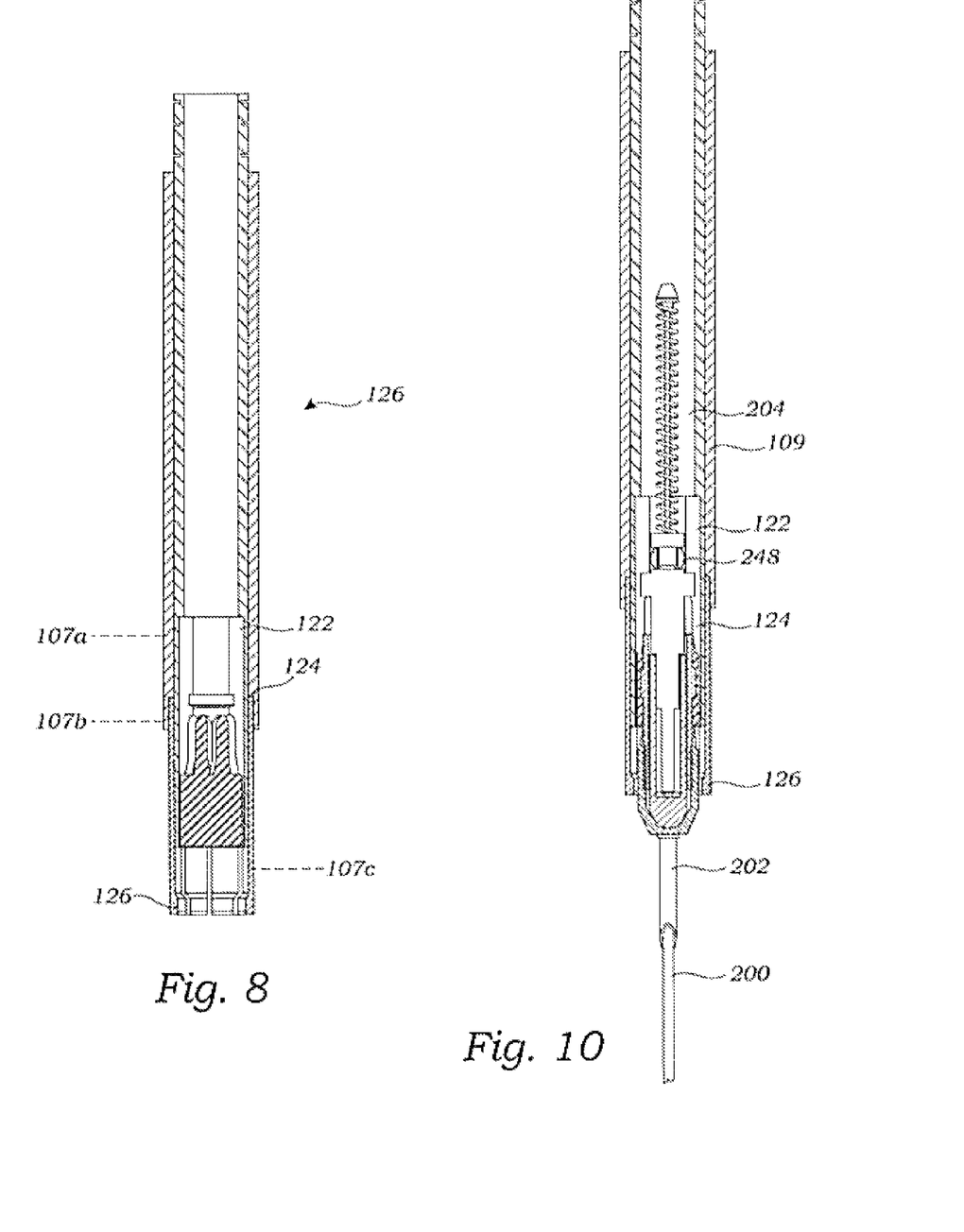
FIG. 8 is a partially cut-away sectional view of a holding unit located within a motor drive assembly in the tool assembly of FIG. 7.
FIG. 10 illustrates the multi-part tool of FIG. 9A operatively engaged with the holding unit of FIG. 8.

FIG. 8 illustrates the holding unit 109 in accordance with some embodiments. The holding unit 109 includes a first engagement portion 122 for engaging a first portion of the cannula assembly 110, a second engagement portion 124 for engaging a second portion of the cannula assembly 110, and a third engagement portion 126 for engaging a third portion of the cannula assembly 110.

Figure 9A:
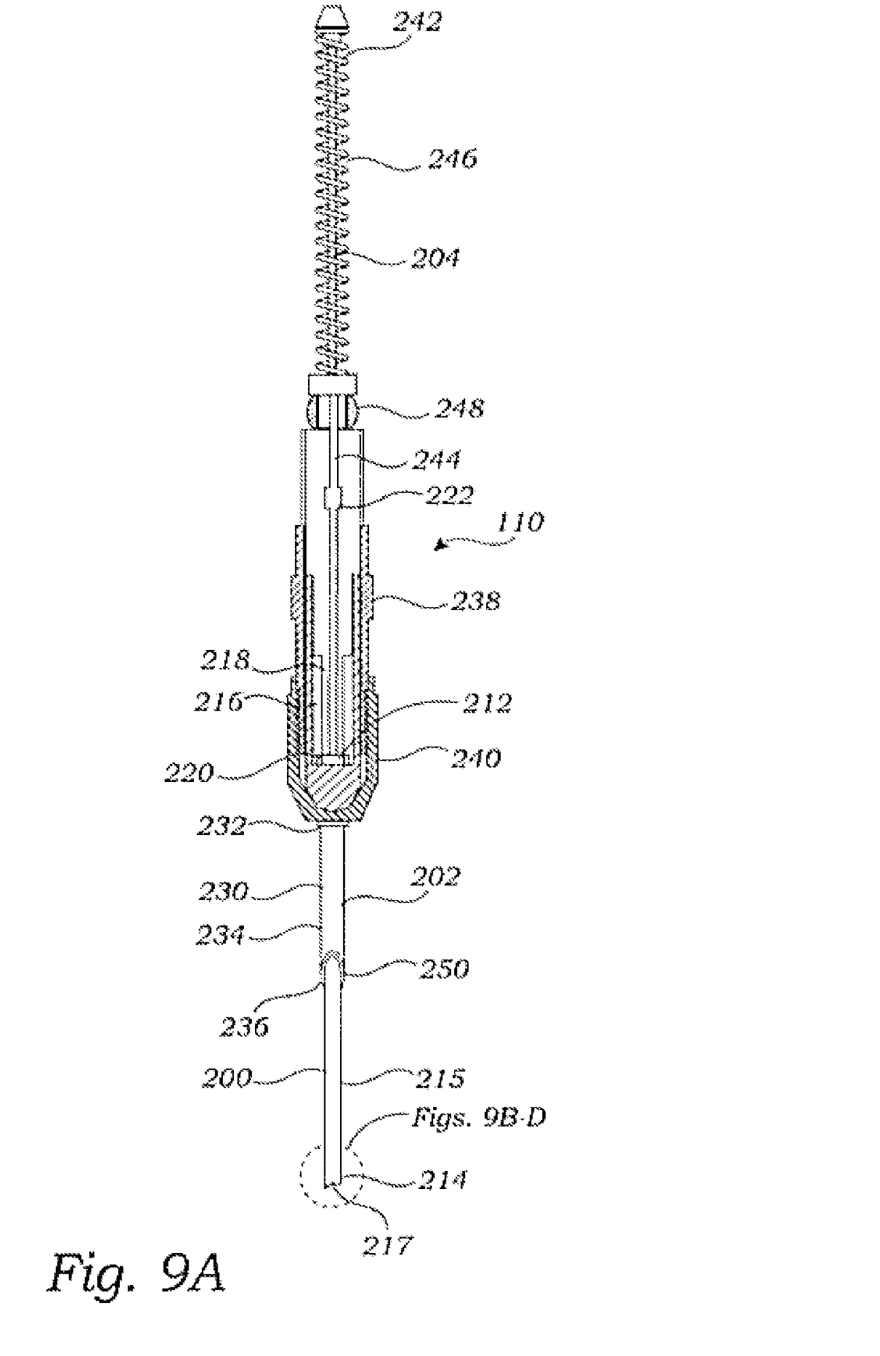
FIG. 9A is a lengthwise sectional view of a multi-part tool for use in the tool assembly in the system of FIG. 7.

FIG. 9A illustrates the cannula assembly 110 in accordance with some embodiments. The cannula assembly 110 has a similar configuration as the tool 32 shown in FIGS. 3-4. The cannula assembly 110 includes a harvesting cannula 200, an implanting cannula 202, and a plunger (obturator) 204. The harvesting cannula 200 has a proximal end 212, a distal end 214, a body 215 extending between the proximal and distal ends 212, 214, and a lumen 217 defined at least partially by the body 215. In the illustrated embodiments, the lumen 217 has a cross sectional dimension that is between 0.3 millimeter and 2.0 millimeters, and more preferably, approximately 1 millimeter. The cannula assembly 110 further includes a shaft 216 having a proximal end 218, a distal end 220, and a lumen 222 extending between the proximal and distal ends 218, 220. The proximal end 212 of the harvesting cannula 200 is secured to the distal end 220 of the shaft 216. The implanting cannula 202 has a proximal end 232, a distal end 234, a body 230 extending between the proximal and distal ends 232, 234, and a lumen 236 within the body 230. The lumen 236 has a cross sectional dimension sized for accommodating at least a portion of the harvesting cannula 200, and for allowing the harvesting cannula 200 to slide relative to the implanting cannula 202. The distal end 234 of the implanting cannula 202 has a sharp tip 250 for piercing tissue.

Figure 9B:
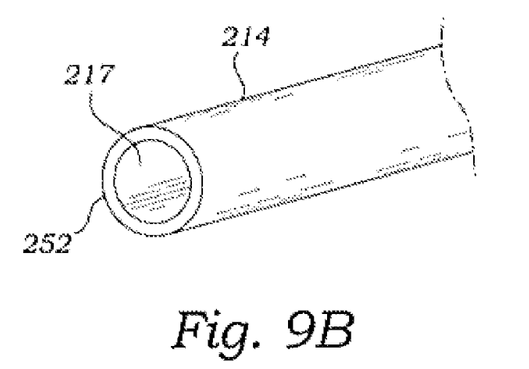
FIGS. 9B-9D illustrate variations of a distal end of a follicular unit harvesting cannula needle of the tool assembly of FIG. 9A.
Figure 9C:
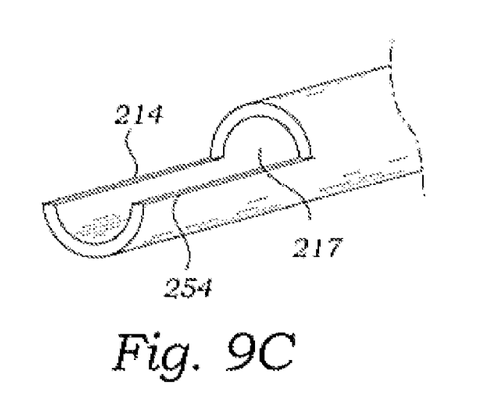
Figure 9D:
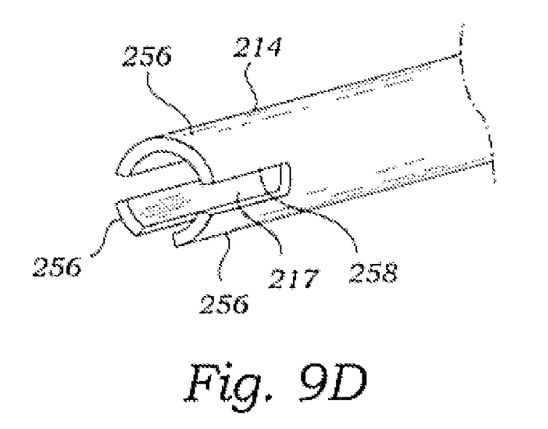

In the illustrated embodiments, the distal end 214 of the harvesting cannula 200 has a tubular configuration (FIG. 9B). In such cases, the edge 252 of the harvesting cannula 200 may have a sharp configuration for allowing the harvesting cannula 200 to penetrate tissue. In other embodiments, the distal end 214 of the harvesting cannula 200 may have an arc configuration (FIG. 9C). In such cases, the ends 254 of the arc portion may have a sharp configuration for allowing the harvesting cannula 200 to cut tissue as the harvesting cannula 200 is rotated about its axis. In further embodiments, the distal end 214 of the harvesting cannula 200 can include a plurality of cutting portions 256, with each cutting portion 256 having a sharp edge 258 for cutting tissue (FIG. 9D). It should be noted that the distal end 214 of the harvesting cannula 200 is not limited to the examples described previously, and that the distal end 214 can have other configurations in other embodiments, as long as it can core tissue.

The cannula assembly 110 further includes a first engagement portion 238 and a second engagement portion 240. The first engagement portion 238 has a tubular configuration, and is secured to the shaft 216. The second engagement portion also has a tubular configuration, and is secured to the proximal end 232 of the implanting cannula 202 proximal end 232 of the implanting cannula 202. The first and the second engagement portions 238, 240 are sized and shaped to engage with corresponding components of the holding unit 109. It should be noted that the first and second engagement portions 238, 240 are not limited to the example of the configuration illustrated, and that the engagement portions 238, 240 can have other configurations in other embodiments. For example, in alternative embodiments, the engagement portion 238 does not have a tubular configuration. In such cases, the engagement portion 238 can be a structure that is secured to, or extends from, a surface of the shaft 216. Similarly, in other embodiments, the engagement portion 240 can be a structure that is secured to, or extends from, a surface of the implanting cannula 202, and needs not have a tubular configuration. As shown in the figure, the cannula assembly 110 also includes a connector 248 secured to the shaft 216. The connector 248 has a shape that resembles a sphere, but may have other shapes in other embodiments.

The plunger 204 has a proximal end 242 and a distal end 244. The plunger 204 is at least partially located within the lumen 217 of the harvesting cannula 200, and is slidable relative to the harvesting cannula 200. The cannula assembly 110 further includes a spring 246 coupled to the plunger 204 for biasing the plunger 204 in a proximal direction relative to the harvesting cannula 200. In the illustrated embodiments, the plunger 204 is described as a component of the cannula assembly 110. In other embodiments, the plunger 204 is not a part of the cannula assembly 110. For example, the plunger 204 may be a component of the positioning assembly 106.

FIG. 10 illustrates the cannula assembly 110 that has been engaged with the positioning assembly 106. When the cannula assembly 110 is snapped onto the positioning assembly 106, the first engagement portion 122 of the holding unit 109 is engaged with the connector 248, the second engagement portion 124 is engaged with the first engagement portion 238 of the cannula assembly 110, and the third engagement portion 126 is engaged with the second engagement portion 240 of the cannula assembly. The connector 248 allows the cannula assembly 110 to be detachably secured to the positioning assembly 106. The first engagement portion 122 of the holding unit 109 is coupled to the first positioner 107a. In some embodiments, the harvesting cannula 200 is not translatable. In alternative embodiments, the first positioner 107a is configured to translate (e.g., advance or retract) the harvesting cannula 200. The second engagement portion 124 of the holding unit 109 is coupled to the second positioner 107b, which is configured to rotate the harvesting cannula 200 about its axis. The third engagement portion 126 of the holding unit 109 is coupled to the third positioner 107c, which is configured to translate (e.g., advance or retract) the implanting cannula 202.

In other embodiments, the second engagement portion 124 of the holding unit 109 may be coupled to both the first positioner 107a and the second positioner 107b. In such cases, the first positioner 107a is configured to translate the engagement portion 124 to thereby advance or retract the harvesting cannula 200, and the second positioner 107b is configured to rotate the engagement portion 124 to thereby turn the harvesting cannula 200 about its axis. In further embodiments, the second positioner 107b is not needed, and the cannula assembly 110 does not include the engagement portion 238. In such cases, the positioning assembly 106 is not configured to rotate the harvesting cannula 200, but to advance and retract the harvesting cannula 200 in a back and forth trusting motion. In still further embodiments, the third positioner 107c is not needed, and the third engagement portion 126 is fixedly secured to the holding unit 109. In such cases, the implanting cannula 202 may be positioned by the robotic arm 27, and the harvesting cannula 200 may be positioned relative to the implanting cannula 202 using the first positioner 107a.

When using the cannula assembly 110 to harvest a follicular unit, the cannula assembly 110 is first coupled to the positioning assembly 106. Such may be accomplished manually by snapping the cannula assembly 110 onto the positioning assembly 106. Alternatively, the cannula assembly 110 may be held upright by a stand (not shown). In such cases, the robotic arm 27 may be used to move the positioning assembly 106 to "grab" the cannula assembly 110 from the stand. The camera(s) 28 may be used to provide information regarding a position of the cannula assembly 110 to the processor 120, which controls the robotic arm 27 based on the information, thereby placing the positioning assembly 106 in engagement position relative to the cannula assembly 110.

Next, a treatment plan is input into the computer 120. In some embodiments, the treatment plan is a prescribed plan designed to transplant hair follicular units from a first region (harvest region) to a target region (implant region). In such cases, the treatment plan may include one or more parameters, such as a number of hair follicular units to be removed/implanted, location of harvest region, location of implant region, a degree of randomness associated with targeted implant locations, spacing between adjacent targeted implant locations, depth of follicle, depth of implant, patient identification, geometric profile of harvest region, geometric profile of implant region, marker location(s), and density of targeted implant locations. Various techniques may be used to input the treatment plan into the computer 120. In the illustrated embodiments, the treatment plan may be input using a user interface that includes a monitor 122 and a keyboard 124. Alternatively, the treatment plan may be input using a storage device, such as a diskette or a compact disk. In other embodiments, the treatment plan may be downloaded from a remote server. In further embodiments, the treatment plan may be input using a combination of the above techniques. For example, some parameters may be input into the computer 120 using a diskette, while other parameters may be input using the user interface. In some embodiments, one or more parameters of the treatment plan may be determined in real time (e.g., during a treatment session).

After the treatment plan has been input into the computer 120, the computer 120 then registers the treatment plan with a patient. In some embodiments, such may be accomplished by using the camera(s) 28 to identify one or more markers on the patient. The marker may be a reflector that is secured to the patient, an ink mark drawn on the patient, or an anatomy of the patient. The identified marker(s) may be used to determine a position and/or orientation of a target region on the patient. In the illustrated embodiments, the treatment plan includes a position of the harvest (or donor) region. Using input from the camera(s) 28, the computer 120 identifies the location of the harvest region on the patient, and a target follicular unit in the harvest region. The computer 120 then operates the robotic arm 27 to place the distal end 214 of the harvesting cannula 200 next to the target follicular unit. In some embodiments, the harvesting cannula 200 is positioned coaxially with the target follicular unit.

Next, the harvesting cannula 200 is used to harvest the target follicular unit. In some embodiments, such may be accomplished by activating a positioner within the positioning assembly 106 to rotate the harvesting cannula 200. As the harvesting cannula 200 is rotated, the harvesting cannula 200 may be advanced distally (e.g., by activating another positioner within the positioning assembly 106, or by moving the positioning assembly 106 using the robotic arm 27). In other embodiments, the harvesting of the target follicle 302 unit may be accomplished by thrusting the harvesting cannula 200 forward and backward. While the harvesting cannula 200 is used to core out the follicular unit 302, the implanting cannula 202 is located proximally away from the distal end 214 of the harvesting cannula 200 to thereby prevent interference with the harvesting procedure. Such may be accomplished by advancing the harvesting cannula 200 distally relative to the implanting cannula 202, or alternatively, by retracting the implanting cannula 202 proximally relative to the harvesting cannula 200 (if the implanting cannula 202 can be positioned).

When the distal end 214 of the harvesting cannula 200 has been advanced within a prescribed depth, e.g., 5 millimeter, below the skin surface, the harvesting cannula 200 is then retracted and removed from the patient. The camera(s) 28 may be used to monitor the harvesting process to thereby determine how far the harvesting cannula 200 has been advanced below the skin surface 306. In some embodiments, the exterior of the harvesting cannula 200 may include marker lines to thereby allow the camera(s) 28 or a physician to "see" how much of the harvesting cannula 200 has been advanced into the patient. In some embodiments, surface friction at the interface between the follicular unit 302 and the interior surface 304 within the lumen 217 will hold the follicular unit 302 as the harvesting cannula 200 is removed from the patient, thereby harvesting the follicular unit 302. In other embodiments, the interior surface 304 can be texturized (e.g., having one or more indents or protrusions) to thereby allow the distal end 214 to more easily hold onto the follicular unit 302 as the harvesting cannula 200 is removed from the patient. In further embodiments, a proximal end of the cannula assembly 110 may be coupled to a vacuum unit (not shown) located within the positioning assembly 106. In such cases, the vacuum unit creates suction within the lumen 217 of the harvesting cannula 200, to thereby pull the target follicular unit 302 away from its underlying tissue as the harvesting cannula 200 is removed from the patient.

Figure 11A:
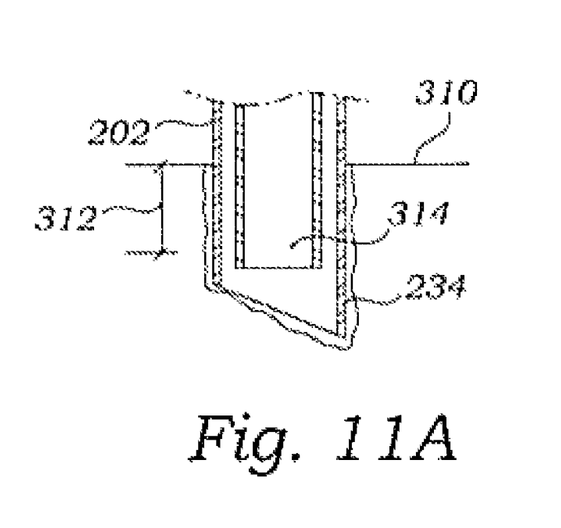
FIGS. 11A-D illustrate a process for implanting a follicular unit, in accordance with some embodiments.

After the follicular unit 302 has been harvested, the positioning assembly 106 retracts the harvesting cannula 200 proximally until the distal end 214 is proximal to the distal end 234 of the implanting cannula 202. Alternatively, if the implanting cannula 202 is positionable, the implanting cannula 202 may be advanced distally until the distal end 234 is distal to the distal end 214 of the harvesting cannula 200. Next, the computer 120 operates the robotic arm 27 to place the distal end 234 of the implanting cannula 202 adjacent to a target location within an implant region of the patient as prescribed by the treatment plan. The implanting cannula 202 is then advanced (e.g., by activating a positioner within the positioning assembly 106, or by moving the positioning assembly 106 distally towards the target location) to pierce through the skin 310 at the implant region (FIG. 11A). The implanting cannula 202 is advanced until the penetrated depth 312 is at least equal to the coring depth 300. In some embodiments, the camera(s) 28 and the computer 120 may be used to determine an amount of the implanting cannula 202 that has been advanced into the patient. For example, the implanting cannula 202 may include a plurality of marker lines for allowing the camera(s) 28 or a physician to "see" how much of the implanting cannula 202 has been inserted into the patient. As shown in the figure, the implanting cannula 202 creates an opening 314 below the patient's skin 314, in which the follicular unit 302 may be placed.

Figure 11B:
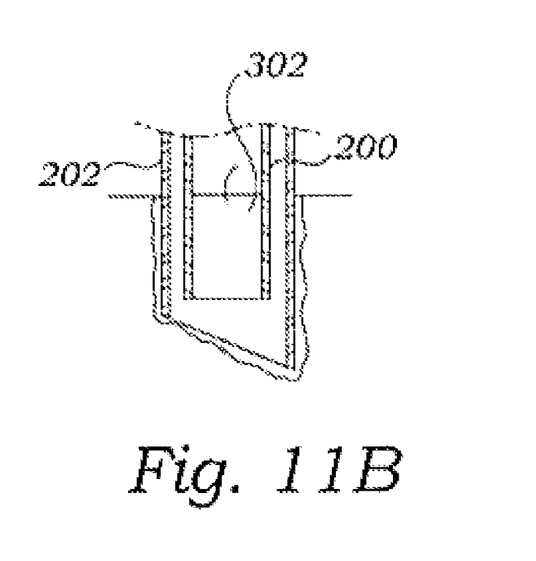
Figure 11C:
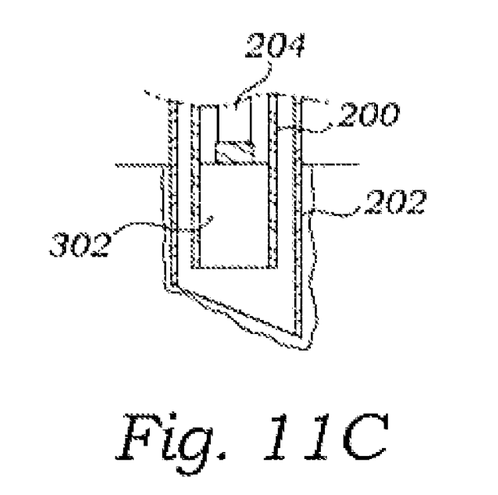
Figure 11D:
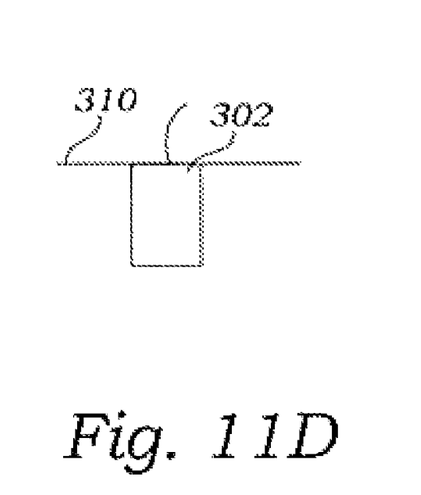

Next, the harvesting cannula 200, which contains the harvested follicular unit 302, is advanced within the lumen 236 of the implanting cannula 202, until a top surface 320 of the follicular unit 302 is at or below the skin 310 at the implant region (FIG. 11B). Next, the plunger 204 may be advanced distally (e.g., by using another positioner within the positioning assembly 106) until its distal end 244 engages with the follicular unit 302 located within the harvesting cannula 200 (FIG. 11C). The implanting cannula 202 and the harvesting cannula 200 are then retracted proximally relative to the plunger 204, thereby leaving the follicular unit 302 implanted at the target location in the implant region (FIG. 11D). In other embodiments, the cannula assembly 110 does not include the plunger 204. In such cases, a pressure generator (not shown) located within the positioning assembly 106 may be used to create a pressure within the lumen 217 of the harvesting cannula 200, thereby pushing the follicular unit 302 towards the patient as the implanting cannula 202 and the harvesting cannula 200 is retracted. Such technique will cause the follicular unit 302 to dislodge from the harvesting cannula 200 while the harvesting cannula 200 is being removed from the patient.

After the first follicular unit 302 has been implanted in the implant region, the harvesting cannula 200 is advanced distally until its distal end 214 is distal to the distal end 234 of the implanting cannula 202. The computer 120 then operates the robotic arm 27 again to place the harvesting cannula 200 next to another target follicular unit 302 to be harvested. The above described process is then repeated to harvest the next follicular unit 302, and to implant the follicular unit 302. The selection of the follicular unit 302 may be determined by the computer 120. For example, in some embodiments, based on a location and geometry of the prescribed harvest region, the computer 120 selects a follicular unit 302 only if it is within the prescribed harvest region. In some embodiments, the above process is repeated until a prescribed number of follicular units 302 have been implanted in the implant region, until a density of the implanted follicle units 302 reaches a prescribed density, or until there is no more available follicular unit 302 in the harvest region.

In some embodiments of the invention employing an automated positioning system, an attending physician or operator may still specify where a follicular unit needs to be implanted and at what angle, i.e., its relative location (or "implantation site"), orientation, and depth. For example, specification of a location, orientation, and/or depth of a follicular unit to be implanted may be carried out by a treatment planning system. Alternatively, during the implanting mode, when the camera(s) are viewing the recipient area of the scalp, the attending operator may use a user interface (e.g., a conventional computer mouse) to specify the implant location and/or position and/or orientation and/or implant depth. Alternatively, the operator can point to location on the scalp by placing a temporary fiducial, such as an ink mark or a pointer that can be visualized, identified, and measured by the image processing system. Further, orientation can be specified directly on the computer monitor as a combination of two angles, such as rotation about x-axis and a rotation about y-axis (assuming that z-axis is along the cannula), or by placing an elongated pointer on the scalp, which the image processing system can visualize and measure the angles.

In any case, the control of the robotic arm now becomes two steps. First, based on the specification of the location and orientation of the implant location, the computer processor directs the robotic arm to move the implanting cannula to a desired location and orientation. Second, the actual advancement of the implanting cannula into the skin surface takes place, either solely by actuating the mechanism, or by a combination of robotic arm movement and mechanism actuation, in which the desired implant depth is achieved. Another way of specifying the orientation of the implanted follicular unit is to have the system match to the orientation of the one or more hair follicles extending there from to the orientation of existing hair follicles in the area of implantation. The system, after positioning the implanting cannula at the implantation location, visualizes and measures the orientation of neighboring hair follicles, and uses this information to determine an appropriate orientation of the follicular unit being implanted. In the case of neighboring hair follicles having different orientations, the system may, for example, obtain a weighted average of the various orientations for determining an orientation of the follicular unit being implanted.

The forgoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. By way of non-limiting example, it will be appreciated by those skilled in the art that the invention is not limited to the use of a robotic system, and that other automated, semi-automated, and manual systems and apparatus may be used for positioning and actuating the respective components of the multi-part tool assembly adjacent the body surface.

What is claimed:

1. An apparatus for harvesting and implanting hair follicular units, comprising:
    an outer implanting cannula having an interior lumen and an open, tissue-piercing distal end configured for implanting a follicular unit into an implant region; and
    an inner harvesting cannula positioned coaxially in the implanting cannula lumen, the inner harvesting cannula having an open, tissue-coring distal end and an interior lumen sized to engage and retain a follicular unit,
    wherein the harvesting and implanting cannulas are moveable relative to each other in a reciprocating relationship, and wherein when harvesting hair follicular units, the distal end of the implanting cannula is located proximal to the distal end of the harvesting cannula.

2. The apparatus of claim 1, further comprising an obturator coaxially positioned in the lumen of the harvesting cannula and independently movable relative to one or both of implanting and harvesting cannulas.

3. The apparatus of claim 1, wherein the apparatus is selected from the group comprising a hand-held device, a substantially automated device, and a device configured to be maneuverable by a robotic system.

4. The apparatus of claim 1, further comprising one or more of a mechanical system, electromechanical system, pneumatic system, hydraulic system and magnetic system for effecting controlled movement of the harvesting and implanting cannulas relative to each other.

5. The apparatus of claim 1, further comprising a motor drive assembly configured for operatively coupling with the implanting and harvesting cannulas for providing automated translational movement of at least one of the implanting and harvesting cannulas relative to the other.

6. The apparatus of claim 5, the motor drive assembly further configured for providing rotational movement of the harvesting cannula about its longitudinal axis.

7. The apparatus of claim 5, further comprising a processor for controlling the motor drive assembly for determining a relative position of the implanting and harvesting cannulas.

8. The apparatus of claim 7, wherein the processor controls the motor drive assembly based at least in part on image data received from one or more cameras.

9. The apparatus of claim 1, further comprising a source of negative pressure in communication with the lumen of the harvesting cannula.

10. The apparatus of claim 8, further comprising a force sensor, and wherein the processor is configured to stop a harvesting or an implanting process if a force sensed by the force sensor exceeds a prescribed limit.

11. An apparatus for harvesting and implanting follicular units, comprising:
    an outer implanting cannula having an open, tissue-piercing distal end and an interior lumen;
    a harvesting cannula positioned in the interior lumen of the implanting cannula, the harvesting cannula having an open, tissue-coring distal end and an interior lumen respectively configured and sized to excise and retain a follicular unit; and
    an obturator positioned in the interior lumen of the harvesting cannula,
    wherein at least one of the implanting cannula, harvesting cannula, and obturator is movable relative to another one of the implanting cannula, harvesting cannula, and obturator, and wherein when harvesting hair follicular units, the distal end of the implanting cannula is located proximal to the distal end of the harvesting cannula.

12. The apparatus of claim 11, wherein the implanting cannula, harvesting cannula, and obturator are coaxially aligned along a common axis and independently movable relative to one another.

13. The apparatus of claim 11, wherein the harvesting cannula is rotatable about its axis.

14. The apparatus of claim 11, wherein the interior lumen of the harvesting cannula is at least partially texturized and sized for receiving a single follicular unit.

15. An apparatus for harvesting and implanting follicular units, comprising:
    an outer implanting cannula having an open, tissue-piercing distal end and an interior lumen;
    a harvesting cannula positioned in the interior lumen of the implanting cannula, the harvesting cannula having an open, tissue-coring distal end and an interior lumen respectively configured and sized to excise and retain a follicular unit; and
    an obturator positioned in the interior lumen of the harvesting cannula,
    wherein the implanting cannula, harvesting cannula, and obturator are coaxially aligned along a common axis and movable relative to one another, and wherein when harvesting hair follicular units, the distal end of the implanting cannula is located proximal to the distal end of the harvesting cannula.

* * * * *

UNITED STATES PATENT AND TRADEMARK OFFICE
CERTIFICATE OF CORRECTION

PATENT NO.      : 7,621,933 B2                                Page 1 of 1
APPLICATION NO. : 11/421438
DATED           : November 24, 2009
INVENTOR(S)     : Bodduluri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 746 days.

Signed and Sealed this

Twenty-sixth Day of October, 2010

David J. Kappos
*Director of the United States Patent and Trademark Office*